United States Patent [19]

Gillig

[11] 4,321,920

[45] Mar. 30, 1982

[54] PERISTALSIS STIMULATING DEVICE

[76] Inventor: H. E. Gillig, 1010 E. Atlantic Bl., Pompano Beach, Fla. 33060

[21] Appl. No.: 155,948

[22] Filed: Jun. 3, 1980

[51] Int. Cl.³ .............................................. A61M 3/00
[52] U.S. Cl. .................................................. 128/239
[58] Field of Search ....................... 128/227, 229, 239

[56] References Cited

U.S. PATENT DOCUMENTS

| | | | |
|---|---|---|---|
| 737,795 | 9/1903 | Woud | 128/239 |
| 1,155,527 | 10/1915 | Sweet | 128/227 |
| 3,916,896 | 11/1975 | Ballard | 128/239 |

*Primary Examiner*—John D. Yasko
*Attorney, Agent, or Firm*—Sherman & Shalloway

[57] ABSTRACT

A peristalsis stimulating device in the form of a jet nozzle having a pyrimidal head designed for insertion in the anus. The nozzle deflects a feather touch fluid stream against the tactile nerve receptors in the lower portion of the rectal ampulla. This activates peristaltic contractions to promote defecation, massage of internal organs and other visceral activity. Accordingly, effective bowel action therapy is provided.

The nozzle is at the distal end of a fluid conveyor tube which is mounted to a seating arrangement. The seating arrangement is placed on a conventional commode and the user sits on the seating arrangement while using the device.

9 Claims, 4 Drawing Figures

PERISTALSIS STIMULATING DEVICE

BACKGROUND OF THE INVENTION

This invention is concerned with a device for providing reflex nerve stimulation for the purpose of activating natural peristaltic contractions. More particularly, the invention concerns a device which is mounted on a seating arrangement for insertion in the user's anus for deflecting fluid against tactile nerve receptors in order to promote the natural peristaltic contractions which result in defecation, as well as natural massage of visceral organs. Several techniques have been used in the prior art for irrigating body cavities. For example, the common bidet is capable of producing either an upwardly-directed or angularly-directed stream of water. However, the previous techniques are not desirable and could be considered dangerous when inserting the nozzle of such devices into a body cavity. Moreover, the nozzles provided with the prior art devices would not be of any use in providing nerve stimulation. Additionally, the bidet is generally in the form of a plumbing fixture and, therefore, must be installed and remain in a single location.

In reviewing the prior art, it has been noted that U.S. Pat. No. 2,427,953 discloses an apparatus for the treatment of rectal disorders having a nozzle attached to a pipe. A nozzle may be inserted within the rectum for internal bath and enema purposes. However, this type of device exhibits considerable complexity including movable supports with gears and shafts. It is also suggested that the cheeks of the patient's rump are spread in order to facilitate the entry of the probing instrument however, there is no suggestion of any means of stimulating the tactile nerve endings for promoting a natural bowel function. Furthermore, U.S. Pat. No. 4,092,894 discloses a device which may be readily removed from the rim of a toilet seat in which an enema tip promotes discharge of waste products. However, this type of device functions by causing the enema tip to reciprocate in and out of the rectum. While such devices may possibly promote a bowel function, the patient usually finds the use of such devices to be very unpleasant.

There have been several proposals for nozzles which provide an outwardly-directed spray within a body opening. For example, U.S. Pat. No. 2,470,293 shows a nozzle wherein a plurality of openings are slanted rearwardly in order to provide a free flow of water or other fluid to affected parts of the opening. However, the nozzle is not disclosed as being stably fixed to any external surface in order to prevent movement of the nozzle.

There has been no teaching in the prior art found that suggests or shows the use and benefits of a nozzle to direct fluid against the tactile nerve endings in an orifice of the body. Accordingly, there has been no teaching found which shows the benefit of the use of such a device for the purpose of exciting a natural synaptic response, bowel function, and natural massage of internal organs, via a tickling spray.

Accordingly, it is an object of this invention to provide a novel means for promoting natural bowel function and subsequent internal massage action. It is a further object to promote natural bowel function by means of providing a stream of fluid such as water to impinge upon the tactile nerve endings, thereby exciting the natural synaptic response which activates peristaltic contractions. It is a further object to provide a jet nozzle that deflects a fluid stream against the tactile nerve receptors of the rectum in the vicinity of the anus in a device which is convenient to use and does not require the assistance of a skilled operator or a helper.

It is a further object to provide such a device which is further adapted for use at the desired site of defecation, such as a commode.

SUMMARY OF THE INVENTION

In accordance with the above-stated objects, there is provided a jet nozzle adapted to be mounted to a fixed surface so that the user may retain the device within a bodily orifice, such as his anus, while it is being used without being required to hold the device in order to retain it within the orifice.

It should be understood that, in accordance with a preferred embodiment of the invention, a fluid conveyor tube is provided with a nozzle at its distal end, the nozzle directing fluid in a fine stream which projects outwardly and away from the distal end so as to impinge upon the tactile nerve receptors of the user's lower rectum. This provides a stimulation which excites the natural synaptic response which activates peristaltic contractions. Further referring to the preferred embodiment, the distal end of the fluid conveyor tube is fitted to a base which supports the user's buttocks and firmly retains the distal end inside his bowel. The base of the device is adapted to be placed on a commode, on a waste-receiving bed, over a bedpan or over any other convenient receptacle.

According to a further aspect of the invention, a nozzle is provided within the distal end of a flexible fluid conveyor tube and the fluid conveyor tube is secured from axial movement by a support on a base. The distal end is provided with a nozzle which projects fluid outwardly and caudally downward from the side of the distal end in order to stimulate the tactile nerve receptors of the user's rectum.

This invention further provides a novel method for stimulating peristaltic contractions by inserting a nozzle into a patient's rectum and spraying fluid from the nozzle caudally downward and radially outward from the nozzle. The fluid is sprayed onto a lower portion of the rectal ampulla in order to excite tactile nerve receptors on that portion. This activity stimulates the peristaltic contractions, visceral actions and defecation.

BRIEF DESCRIPTION OF THE DRAWING

The invention will be better understood from the following detailed description when read in conjunction with the drawing wherein.

DETAILED DESCRIPTION OF THE PREFERRED EMBODIMENT

Figure 1:
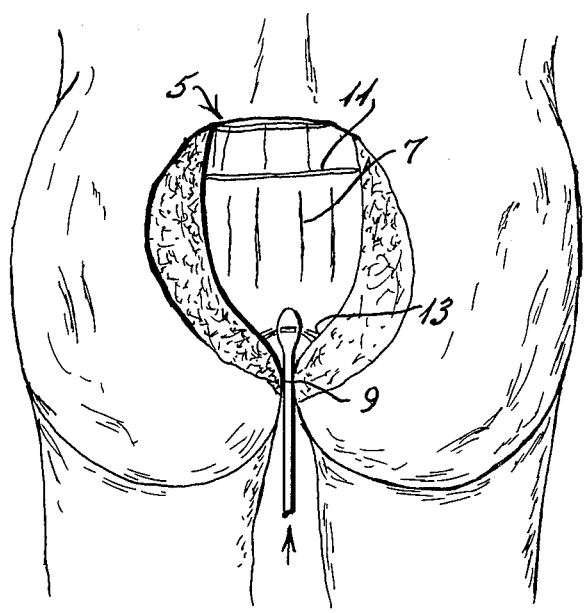
FIG. 1 illustrates an end portion of a preferred embodiment of the invention inserted for use.

FIG. 1 is a schematic representation of the human intestinum rectum (rectum) 5. The rectum 5 consists of a dialated portion known as the rectal ampulla 7 which forms the lower end of the large intestine, and the anal canal or anus 9. When fecal material (not shown) passes from the large intestine it enters the rectal ampulla 7 causing the rectal ampulla 7 to distend. The rectal ampulla 7 has formed therein folds known as Houston's valves 11 which tend to discourage the fecal matter from urging toward the anus 9. As the quantity of fecal matter increases, the rectal ampulla 7 distends and the fecal matter presses against a lower portion 13 which forms the lower end of the rectal ampulla 7. At this point the tactile nerve receptors on the lower portion 13 of the rectal ampulla 7 cause a synaptic nerve response which activates peristaltic contraction of muscles surrounding the rectum. Thus, fecal material is discharged through the anus 9.

Figure 2:
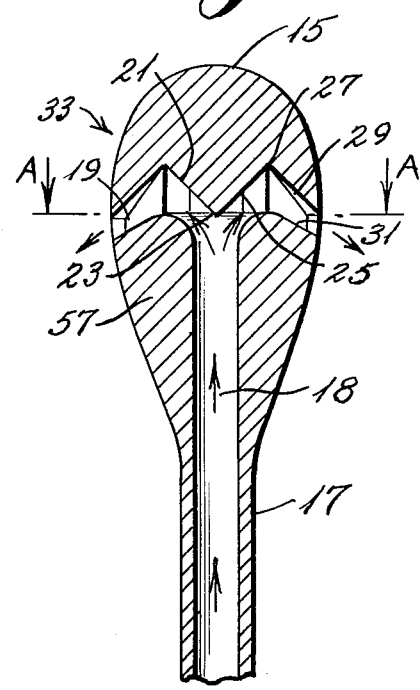
FIG. 2 illustrates a cross section of the end portion of a preferred embodiment of the invention.
Figure 3:
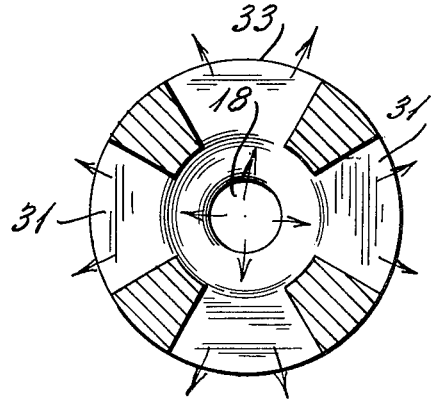
FIG. 3 is a cross-sectional view of a nozzle according to the preferred embodiment of the invention taken along lines A—A of FIG. 2.

Referring to FIGS. 1-3, the peristalsis stimulating device, according to this invention, has a distal end 15 mounted on the end of a fluid conveyor tube 17. The interior 18 of the fluid conveyor tube 17 communicates with a nozzle 19 near the distal end 15. The nozzle 19 is constructed generally of an inverted pyramidal deflector 21 having a vertex 23 at the center, and the sides 25 of the pyramidal deflector 21 sloping outwardly and in the direction of the distal end 15. Thus, when fluid impinges upon the pyramidal deflector 21, the fluid is turned outwardly but is not initially reversed in direction. At a portion 27 of the sides 25 furthest from the vertex 23, a terminal portion 29 extends away from the distal end 15. Opposite the terminal portion is a converging surface 31 which, together with the terminal portion 29 forms a converging nozzle directing fluid outwardly and away from the distal end 15. The nozzle 19 is contained within a bulb-shaped nozzle body 33 which is faired into the fluid conveyor tube 17.

With reference to FIG. 1, the distal end 15 is inserted in the user's anus 9 until the nozzle body 33 has entered the rectal ampulla near the lower portion 13 of the rectal ampulla 7.

A constant stream of fluid is provided to the fluid conveyor tube 17 and the fluid exits the nozzle 19. With the nozzle body 33 in the rectal ampulla 7 adjacent to the anus 9 the fluid impinges upon the lower portion 13 of the rectal ampulla 7. This performs three functions. Firstly, the fluid stream exiting from the nozzle 19 impinges upon the tactile nerve receptors located in the lower portion 13 of the rectal ampulla 7, adjacent to the upper portion of the anus 9. These nerve endings are from the Inferior Mesenteric Plexus (P. Rectalis s.) from the Pelvic Plexus (P. Rectalis medius) and from the Pudenteal Plexus (P. Rectalis inferioris). The fluid impinging on the tissue compresses or "tickles" the tissue, thus stimulating the nerve receptors which results in a synaptic reflex response which activates peristaltic contractions of the muscles surrounding the colon and rectum. This contraction is the body's bowel elimination response. Secondly, the fluid performs an enema function including the softening of fecal matter and the provision of fluid lubrication facilitating the passage of fecal matter through the anus 9. Finally, the fluid may be used to medicate the rectum, providing treatment for a variety of disorders.

Unlike, and in contrast to, a conventional enema, the present invention encourages peristaltic contractions, thereby training the patient's body to naturally eliminate. In partially paralyzed patients where a potential of nerve response exists, this training can be invaluable. Thus the patient can be trained to provide a natural elimination response with a reduced amount of additional biofeedback.

The ability to stimulate the tactile nerve receptors in the lower portion 13 of the rectal ampulla adjacent the anus 9 enables a patient to eliminate at will when elimination is desired. The device may, therefore, be used to artificially evoke the natural synaptic response by the fluid. This procedure may, in many instances, eliminate the need for a bedpan.

It should be understood that it is desirable to retain the fluid conveyor tube 17 with the nozzle body 33 in the desired position adjacent the upper portion of the anus 9 without requiring that the patient or any assistant hold the fluid conveyor tube 17. This is particularly important because the purpose of the device is to evoke defecation. Moreover, the device should not extend too far into a patient's rectum so that the fluid from the nozzle can be directed at the proper end bulb's location. Defecation and the peristaltic contractions tend to evict the fluid conveyor tube; to prevent this, the tube is fixed to a seating arrangement which may be placed on a waste receptacle such as a commode.

Figure 4:
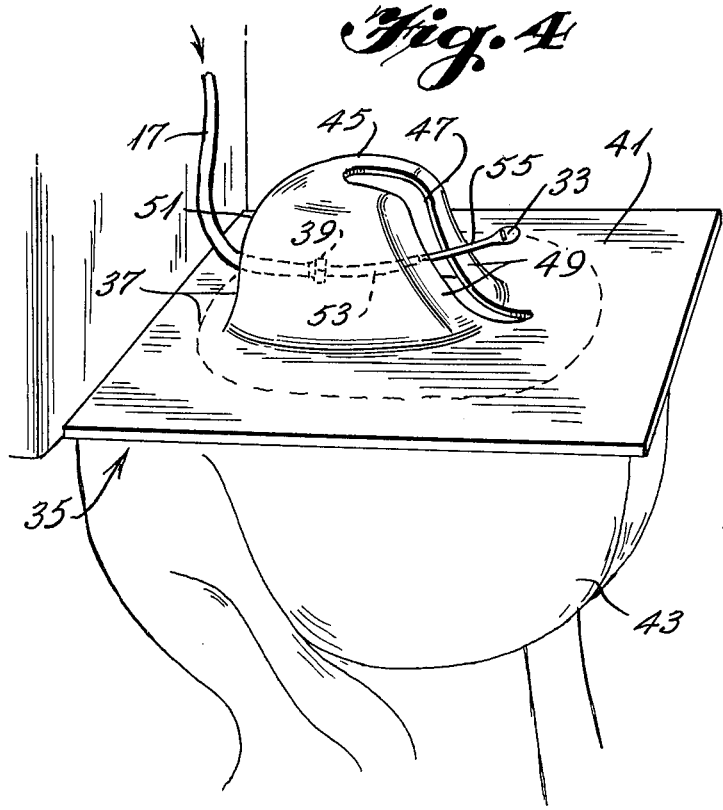
FIG. 4 illustrates a seating arrangement according to the preferred embodiment of the invention.

With reference to FIG. 4, the seating arrangement 35 consists of a molded body 37 with a bracket 39 which functions to maintain the fluid conveyor tube 17 in a relatively fixed position with respect to the moded body 37. The bracket 39 may be any conventional tube-holding means, such as a hole which is slightly smaller than the fluid conveyor tube 17 drilled through the molded body 37, said body 37 consisting of a relatively flat portion 41 adapted to rest on a top surface of a waste receptacle such as a conventional commode 43.

Within the flat portion 41, and surrounded thereby, is a raised portion 45. An opening 47 is provided in the raised portion 45 and the opening 47 may extend beyond the raised portion 45 to the flat portion 41. On either side of the opening 47 are concave buttock-receiving surfaces 49 which act as a seat for the patient. The opening 47 which extends between the buttock-receiving surfaces 49 provides a passage for the patient to defecate into the commode 43.

The bracket 39 is located behind the buttock-receiving surface and when the seating arrangement 35 is placed on the commode 43, and behind the buttock-receiving surface 49, the fluid conveyor tube 17 passes through a rear section 51 of the raised portion 45 and the fluid conveyor tube 17 is positioned by the bracket 39 so that the nozzle body 33 extends through the opening 47 and above the buttock-receiving surface 49.

The fluid conveyor tube 17 consists of a flexible tube 53 such as vinyl surgical tubing which is joined near the nozzle body 33 to a semi-rigid portion 55. The semi-rigid end portion is preferably molded integrally with that portion 57 of nozzle body 33 having the converging surface 31.

Thus, it can be seen that a patient may insert the nozzle body 33 into his anus 9 as he proceeds to rest his buttocks against the buttock-receiving surface 49. The fluid conveyor tube 17 is so positioned by the bracket 39 in relation to the buttock-receiving surface 49 that the nozzle body 33 will be retained in the proper position in rectum 5 adjacent the lower portion 13 of the rectal ampulla 7.

Water or other fluid may then be provided through the fluid conveyor tube by conventional means (not shown) such as a diverter attachment fixed to a water tap, a water bag or a pump and tank arrangement. However, the fluid conveyor tube 17 may be further used to provide a cleansing function after use in the rectum 5 by providing a continued liquid flow through the nozzle 19 while the patient is unseating himself. This is made possible by the fact that the fluid conveyor tube 17 is fixed to the seating arrangement 35 by the bracket 39. It can thus be seen that a device has been provided which may be used for promoting a natural function by the stimulation of nerve endings with a fluid spray. The device has been described in connection with bowel elimination, however the novel device of the subject invention may also be used for the irrigation or stimulation of other body cavities such as stomas or the vagina. Thus, modifications may be made to the device without departing from the inventive concepts. For example, it would be possible to provide a lounge-like backrest (not shown), hingably fixed to the seating arrangement 35, so as to permit a comfortable reclining distribution of body weight while the buttock-receiving surfaces 49 maintain the patient's buttocks fitting snugly at the central opening 47. Such a hinged backrest could then be folded toward the seating arrangement 35, so that the device could be conveniently stowed.

What is claimed is:

1. A peristalsis-stimulating device for activating muscles of a relatively unrestricted body cavity forming the intestinam rectum comprising:
   (a) a seating arrangement adapted to be placed on a waste receptacle;
   (b) a fluid conveyor tube having a distal end that can be readily adapted to being inserted up the body cavity, the fluid conveyer tube having an outer profile which is sufficiently narrow to permit spontaneous evacuation by a patient when the tube is in said patient's anal canal;
   (c) a nozzle located within the distal end, the nozzle being located with respect to the seating arrangement and adapted to deflect a fluid stream radially outwardly and candally downwardly away from the distal end toward tactile nerve receptors within the cavity for the purpose of stimulating the nerve receptors, whereby
   the fluid stream directed toward the tactile nerve receptors lightly touches said nerve receptors, and thereby evokes peristaltic contraction of the muscles surrounding the rectum, permitting and causing bowel elimination while the fluid conveyor tube is in the patient's anal canal.

2. The device of claim 1 wherein said waste receptacle is a commode.

3. The device of claim 1 wherein said seating arrangement further comprises:
   (a) a flat portion adapted to rest on a support surface of the waste receptacle;
   (b) a raised portion fixed to the flat portion, the raised portion having buttock-receiving surfaces thereon;
   (c) a central opening with said distal end of nozzle extending from the central opening.

4. The device of claim 1 wherein the seating arrangement comprises:
   (a) a flat portion adapted to rest selectively on relatively flat support surfaces of a commode, a bedpan, a waste-receiving patient bed, a bidet or another waste receptacle;
   (b) a raised portion fixed to the flat portion, the raised portion having buttock-receiving surfaces thereon;
   (c) a central opening with said distal end of nozzle extending from the central opening.

5. The device of claims 1, 2, 3 or 4 wherein:
   (a) said cavity is the user's rectum;
   (b) said distal end is positioned on said seating arrangement so that said distal end is readily received by the user's anus when the user sits on said seating arrangement; and
   (c) said nozzle deflects said fluid stream to impinge against a portion of the user's rectal ampulla adjacent said anus, thereby compressing said portion and producing tactile stimulation of said nerve receptors.

6. A method for stimulating a natural synaptic response which activates peristaltic contractions of the colon comprising:
   (a) directing a fluid stream through a fluid conveyor tube;
   (b) causing the stream to exit radially outward and caudally downward from the distal end of the said irrigation tube;
   (c) positioning said distal end within the rectum of a user so that said fluid stream lightly impinges upon a lower portion of the user's rectal ampulla so that said fluid stimulates nerve receptors located on said lower portion of the rectal ampulla by exerting a compressive effect upon said portion, thereby exciting nerve receptors in said portion, said positioning being effected by mounting that fluid conveyer tube to a seating arrangement;
   (d) permitting evacuation when the distal end is inserted up the user's anus.

7. A method of claim 6 wherein the fluid conveyor is mounted to a seat in order to effect said positioning of a distal end within the rectum.

8. A spraying device for tickling rectal nerve endings for the purpose of evoking natural synpatic response resulting in peristaltic contractions of the muscles surrounding the colon and rectal ampulla comprising:
   (a) a seating arrangement with a flat portion adapted to rest on a support surface of a waste receptacle, a raised contoured portion fixed to the flat portion, the raised contoured portion having buttock-receiving surfaces thereon, and a central opening that permits protrusion of a portion of the nozzle as needed for the variations in buttock dimensions;
   (b) a fluid conveyor tube having a distal end adapted to be inserted into the body cavity forming the intestinum rectum, said distal end extending from said central opening; and the fluid conveyor tube having an outer profile which is sufficiently narrow to permit spontaneous evacuation by a patient when the tube is in said patient's anal canal;
   (c) a nozzle located within the distal end, the nozzle being adapted to deflect a constant spray or stream of fluid radially outward and caudally downward away from the distal end toward said tactile nerve receptors for the purpose of stimulating the nerve receptors, whereby
   the fluid stream directed toward the tactile nerve receptors evokes peristaltic contraction of the muscles surrounding the rectum, permitting and causing bowel elimination while the fluid conveyor tube is in the patient's anal canal.

9. The device of claim 8 wherein said distal end is a disposable unit readily separable from the remainder of the fluid conveyor tube.

* * * * *